United States Patent [19]

Campbell

[11] 4,139,721

[45] Feb. 13, 1979

[54] PROCESS FOR PREPARING DIPHENYL HALOETHYLENES

[75] Inventor: John R. Campbell, Clifton Park, N.Y.

[73] Assignee: General Electric Company, Schenectady, N.Y.

[21] Appl. No.: 901,515

[22] Filed: May 1, 1978

[51] Int. Cl.$^2$ ................. C07C 37/00; C07C 41/00
[52] U.S. Cl. ..................................... 568/641; 568/726
[58] Field of Search ................... 568/726; 260/613 R

[56] References Cited

U.S. PATENT DOCUMENTS

| | | | |
|---|---|---|---|
| 3,247,265 | 4/1966 | Speziale et al. | 260/613 R X |
| 3,642,910 | 2/1972 | Holan | 260/613 R |
| 3,663,602 | 5/1972 | Steinmann | 260/613 R X |
| 3,760,007 | 9/1973 | Steinmann | 260/613 R X |
| 3,991,120 | 11/1976 | Ladd | 260/613 R |
| 4,073,814 | 2/1978 | Kinson et al. | 568/726 |

*Primary Examiner*—Bernard Helfin
*Attorney, Agent, or Firm*—Joseph T. Cohen; Charles T. Watts

[57] ABSTRACT

Diphenyl chloroethylenes are prepared by the reaction of either phenol or anisole with a trihaloethylene compound.

10 Claims, No Drawings

PROCESS FOR PREPARING DIPHENYL HALOETHYLENES

This invention is concerned with a process for preparing diphenyl haloethylenes. More particularly, the invention is concerned with a process for making a diphenyl haloethylene compound of the general formula

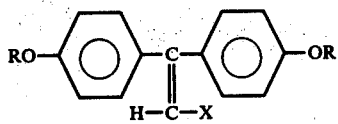

which comprises effecting reaction between an aryl compound of the general formula

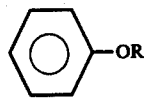

with a haloethylene compound of the general formula $$X_2C = CHX \qquad \text{III}$$

in the presence of trifluoromethanesulfonic (triflic) acid and isolating the aforesaid diphenyl haloethylene compound, where R is a member selected from the class consisting of hydrogen and the methyl radical, and X is a member selected from the class consisting of chlorine and bromine.

Compounds of formula I where R is hydrogen, can be treated with a phosgenating agent such as phosgene or diphenyl carbonate to make polycarbonate resins (as described in Polish Pat. No. 48,893 issued Dec. 12, 1964) which have good impact characteristics and flame-retardant properties. These properties recommend that such polymers be used in various molding and coating applications, such as housings for electric equipment, grills for automobiles, etc. Compounds of formula I, where R is a methyl radical, can be used as pesticides similar to that for which DDT is employed. Additionally, such compounds can be employed as intermediates for making compounds of formula I, where R is hydrogen, by treating the dimethoxy derivatives with suitable agents in a manner well known in the art to convert the OR groups to OH groups, which can then be converted to polycarbonate resins as described above.

Compounds of formula I, where R is hydrogen, are generally prepared by a two-step process involving a condensation of dichloroacetaldehyde diethylacetal and phenol in the presence of an acidic condensing agent, such as sulfuric acid, followed by dehydrochlorination of the intermediate saturated dichloroethylene compound. While the final monomer which in the case where X is chlorine, having the formula

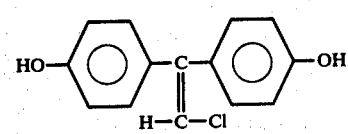

is obtained in acceptable yield by this route, substantial amounts of by-products are obtained in the form of the ortho, para-isomer (two stereoisomers) of the formulas

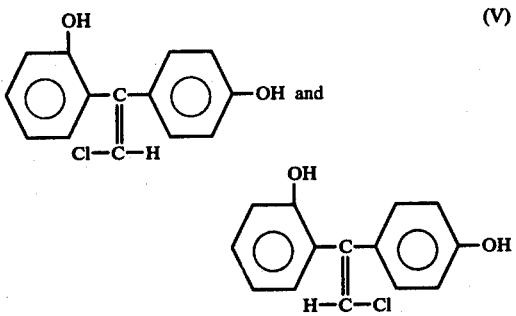

In addition to these ortho, para-isomers having possible harmful effects on polymers made from the para, para-isomer, this process also uses an expensive starting material, namely, the dichloroacetaldehyde diethylacetal that is not readily available at present. Furthermore, before one can obtain the monochloroethylene dihydroxydiphenyl compound, it is necessary to subject the precursor dichloro-ethane compound of the formula

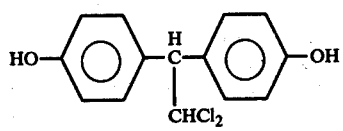

to a dehydrohalogenation step to form the compound having the formula IV. All the foregoing defects in using prior art methods for making the dihydroxy compound embraced by general formula I, and particularly the compound of formula VI add to the cost and complexity of not only obtaining the monomer but also ultimately obtaining any polymer derived therefrom.

Unexpectedly, I have discovered that I am able to make compounds of the general formula I in essentially a one-step process by effecting reaction between either phenol or anisole with a trichloroethylene compound (e.g., trichloroethylene, tribromoethylene, 1,1-dichloro-2-bromoethylene, etc.) in the presence of trifluoromethanesulfonic acid employing relatively mild conditions. In addition to forming the monochloroethylene compound of formula I directly, the amount of the ortho, para-isomer is quite small and can be readily removed and treated with the trifluoromethanesulfonic acid again to isomerize the ortho, para-isomer to additional yields of the para, para-isomer. In addition to the above, the yields of the para, para-isomer are generally in the range of 50 to 75%.

It was entirely unexpected and in no way could have been predicted that the use of trifluoromethanesulfonic acid with the trichloroethylene and either the phenol or anisole would give the products described above since attempts to apply the same process to the reaction of, for instance, phenol with tetrachloroethylene, did not give evidence of any formation of the dihydroxydiphenyl dichloroethylene compound of formula

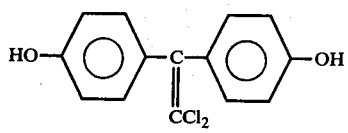

VII

The reaction between the aryl compound of formula II and the haloethylene compound of formula III is advantageously carried out under atmospheric pressures (although superpressures are not precluded) employing at least 2 mols of the formula III compound per mol of the aryl compound of formula II. Excess molar quantities of the haloethylene compound up to 15 or more mols per mol of the aryl compound may be used without departing from the scope of the invention.

The temperature of the reaction is not critical and can be varied widely; thus, temperatures of from about 10° to 100° C. can be advantageously employed. Usually temperatures of from 25° to 75° C. are adequate for the purpose since the reaction is exothermic and may require cooling in order to avoid excessive heating of the reaction mixture. The time of reaction can also be varied widely, ranging from about 1 hour to 36 hours or more, depending on the temperature at which the reaction is carried out, the proportion of ingredients, the particular aryl compound used, etc.

The amount of trifluoromethanesulfonic acid used can be quite small and may range on a weight basis from about 0.5 to 3 parts or more of the triflic acid per part of the aryl compound of formula II.

Inert solvents may also advantageously be employed in the practice of the invention, although they are usually unnecessary. Among such inert solvents may be mentioned methylene chloride, chloroform, dichloroethane, etc. The choice of the solvent medium is not critical as long as the solvent medium is liquid and is inert to the reactants and to the reaction products. Also, the solvent medium should have a boiling point sufficiently low to enable the solvent to be removed readily during isolation of the desired compound. An inert atmosphere, such as a nitrogen atmosphere, is helpful in order to minimize any side reactions.

In order that those skilled in the art may better understand how the present invention may be practiced, the following examples are given by way of illustration and not by way of limitation. In all instances a nitrogen atmosphere was maintained over the reacting ingredients together with stirring conditions.

The determination of the amount of para, para-isomer obtained in the following examples was carried out by silylation of the reaction mixture containing the enhanced amounts of para, para-isomer with bis(trimethylsilyl) acetamide in the manner described by Klebe et al. in J.A.C.S. 88, 3390 (1966) and then analyzed by vapor phase chromatography using a 6′ × ⅛″ Se-30 column with a temperature program of 200° to 300° C. at 10° C. per minute. VPC retention times for the ortho, para-isomer compound and the para, para-isomer compound are 5.0 and 6.1 minutes, respectively.

EXAMPLE 1

A mixture consisting of 30 grams (0.229 mol) trichloroethylene, 3.5 grams (0.0372 mol) phenol, and 7.5 grams triflic acid was heated with stirring at a temperature of about 70° C. for varying lengths of time. Samples were taken from the reaction mixture periodically, treated successively with bis(trimethylsily) acetamide, and then with tetramethyl urea and analyzed in the manner described above. These analyses showed the presence of the para, para-isomer of formula IV and the two stereo ortho, para-isomers of formula V. The following Table I shows the results of carrying out this reaction by means of the percent conversion of the three isomers based on the amount of phenol used.

TABLE 1

| Time (minutes) | Para, Para-Isomer Formula IV | Combined Ortho, Para-Isomers Formula V |
|---|---|---|
| 95 | 1.6 | 1.1 |
| 352 | 12.4 | 1.3 |
| 780 | 29.8 | 1.0 |
| 900 | 30.1 | 1.4 |
| 1035 | 36.2 | 2.2 |
| 1110 | 44.1 | 3.6 |
| 1300 | 45.5 | 4.9 |
| 1490 | 40.0 | 6.0 |
| 1740 | 31.2 | 7.7 |

EXAMPLE 2

When 210.0 mg. (1.6 mmol) trichloroethylene, 110.0 mg. (1.17 mmol) phenol, and 3.0 grams triflic acid (so that the trichloroethylene was in excess) were reacted similarly as in Example 1 at 25° C., it was found that after about 4 hours a yield of 19.6% conversion to the para, para-isomer of formula IV based on the phenol was obtained, while the combined mixture of the two ortho, para-isomers of formula V comprised an 8.4% conversion, again based on the phenol.

EXAMPLE 3

In this example, 100 mg. (1.06 mmol) phenol, 600 mg. (2.29 mmol) tribromoethylene, and 1.9 grams triflic acid were reacted and analyzed similarly as described in Example 1 with the exception that the reaction was carried out at 25° C. After about 20 minutes, the sample was analyzed as previously described to establish a yield based on the phenol of about 13% of the bromoethylene compound of formula

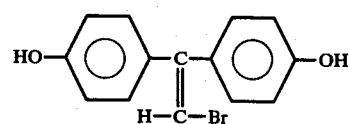

VIII and about 7% of the mixture of the two ortho, para-stereoisomers of the formula

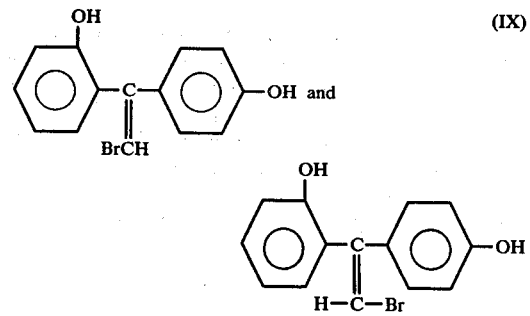

EXAMPLE 4

Employing the conditions of Example 1 but carrying out the reaction at a temperature of about 25° C. for varying lengths of time, 308.1 mg. (2.8 mmol) anisole, 1.5044 grams (11.0 mmol) trichloroethylene, and 9.0075 grams triflic acid were reacted and the reaction product analyzed and found to contain varying amounts, depending on the time of reaction, of the dimethoxychloroethylene compound of the formula

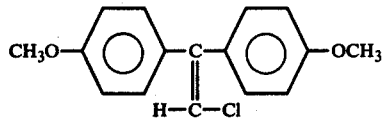

X and the two ortho, para-stereoisomers having the formulas

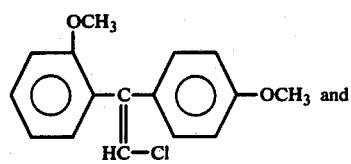

(XI)

The following Table II shows the percent conversion (based on anisole) of the para, para-isomer and the total ortho, para-stereoisomers as a function of time.

TABLE II

| Time (hours) | Percent Conversion | |
| --- | --- | --- |
| | Para, Para-Isomer | Combined Ortho, Para-Stereoisomers |
| 1.75 | 24 | 13 |
| 3.17 | 33 | 16 |
| 4.5 | 37 | 15 |
| 6.7 | 40 | 11 |

EXAMPLE 5

Employing the same conditions as described in Example 1 but using a temperature reaction of about 25° C., 72.5 mg. (0.67 mmol) anisole, 510.3 mg. (1.90 mmol) tribromoethylene, and 1.042 grams triflic acid were reacted for 8 hours and the reaction product analyzed as described above. Analysis showed the presence of the para, para-isomer having the formula

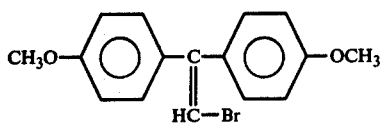

XII and the two ortho, para-stereoisomers corresponding to the formulas

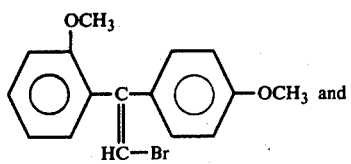

XIII

-continued

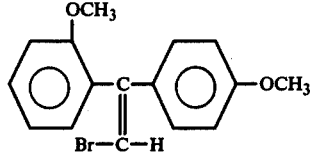

The yields of the three isomers and particularly the para, para-isomer, were essentially the same as those found for the three isomers in Example 3.

It will of course be apparent to those skilled in the art that in addition to the conditions under which the foregoing examples were carried out, other conditions of reaction can be employed in accordance with the above description. Moreover, within the scope of the intended invention, the amount and ratio of ingredients employed can also be varied as is evident from the examples given above.

What I claim as new and desire to secure by Letters Patent of the United States is:

1. The process for making a diphenyl haloethylene compound of the general formula

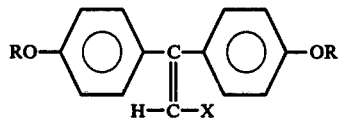

which comprises effecting reaction between an aryl compound of the general formula

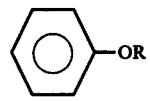

with a haloethylene compound of the general formula $X_2C = CHX$ in the presence of trifluoromethanesulfonic acid and thereafter isolating the aforesaid diphenyl haloethylene compound, where R is a member selected from the class consisting of hydrogen and the methyl radical, and X is a member selected from the class consisting of chlorine and bromine.

2. The process as in claim 1, wherein the aryl compound is phenol.

3. The process as in claim 1, wherein the aryl compound is anisole.

4. The process as in claim 1, wherein the haloethylene compound is trichloroethylene.

5. The process as in claim 1, wherein the haloethylene compound is tribromoethylene.

6. The process as in claim 1, wherein the aryl compound is phenol and the haloethylene compound is trichloroethylene.

7. The process as in claim 1, wherein the aryl compound is phenol and the haloethylene compound is tribromoethylene.

8. The process as in claim 1, wherein the aryl compound is anisole and the haloethylene compound is trichloroethylene.

9. The process as in claim 1, wherein the aryl compound is anisole and the haloethylene compound is tribromoethylene.

10. The process as in claim 1, wherein the reaction is carried out at a temperature of from about 10° to 100° C.

* * * * *